(12) United States Patent
Kim et al.

(10) Patent No.: US 7,189,392 B1
(45) Date of Patent: Mar. 13, 2007

(54) INJECTABLE CARRIER FORMULATIONS OF HYALURONIC ACID DERIVATIVES FOR DELIVERY OF OSTEOGENIC PROTEINS

(75) Inventors: Hyun Kim, Middleton, MA (US); Rebecca Li, Bedford, MA (US); Alessandra Pavesio, Padua (IT); Lanfranco Callegaro, Thiene (IT); Howard Seeherman, Cambridge, MA (US); John Wozney, Hudson, MA (US)

(73) Assignees: Genetics Institute, LLC, Cambridge, MA (US); Fidia Advanced Biopolymers S.R.L., Abano Terme (IT)

( * ) Notice: Subject to any disclaimer, the term of this patent is extended or adjusted under 35 U.S.C. 154(b) by 0 days.

(21) Appl. No.: 09/687,281

(22) Filed: Oct. 13, 2000

Related U.S. Application Data

(60) Provisional application No. 60/159,674, filed on Oct. 15, 1999, provisional application No. 60/185,587, filed on Feb. 28, 2000.

(51) Int. Cl.
*A61K 38/43* (2006.01)
(52) U.S. Cl. .................................................. 424/94.1
(58) Field of Classification Search .................. 514/21, 514/23; 424/423, 94.1
See application file for complete search history.

(56) References Cited

U.S. PATENT DOCUMENTS

| | | | |
|---|---|---|---|
| 2,465,357 A | 3/1949 | Correll et al. | |
| 3,955,719 A * | 5/1976 | Pheulpin | 222/386 |
| 4,191,747 A | 3/1980 | Scheicher | |
| 4,294,753 A | 10/1981 | Urist | |
| 4,394,370 A | 7/1983 | Jeffries | |
| 4,399,216 A | 8/1983 | Axel et al. | |
| 4,419,446 A | 12/1983 | Howley et al. | |
| 4,434,094 A | 2/1984 | Seyedin et al. | |
| 4,441,915 A | 4/1984 | Arndt et al. | |
| 4,455,256 A | 6/1984 | Urist | |
| 4,468,464 A | 8/1984 | Cohen et al. | |
| 4,472,840 A | 9/1984 | Jefferies | |
| 4,553,542 A | 11/1985 | Schenck et al. | |
| 4,563,350 A | 1/1986 | Nathan et al. | |
| 4,596,574 A | 6/1986 | Urist | |
| 4,608,199 A | 8/1986 | Caplan et al. | |
| 4,619,989 A | 10/1986 | Urist | |
| 4,627,982 A | 12/1986 | Seyedin et al. | |
| 4,642,120 A | 2/1987 | Nevo et al. | |
| 4,662,884 A | 5/1987 | Stenaas | |
| 4,681,763 A | 7/1987 | Nathanson | |
| 4,703,008 A | 10/1987 | Lin | |
| 4,727,028 A | 2/1988 | Santerre et al. | |
| 4,737,578 A | 4/1988 | Evans | |
| 4,758,233 A * | 7/1988 | Phillips et al. | 604/232 |
| 4,761,471 A | 8/1988 | Urist | |
| 4,766,067 A | 8/1988 | Biswas et al. | |
| 4,767,628 A | 8/1988 | Hutchinson | |
| 4,769,328 A | 9/1988 | Murray et al. | |
| 4,774,228 A | 9/1988 | Seyedin et al. | |
| 4,774,322 A | 9/1988 | Seyedin et al. | |
| 4,784,055 A * | 11/1988 | Langen et al. | 99/533 |
| 4,789,732 A | 12/1988 | Urist | |
| 4,795,804 A | 1/1989 | Urist | |
| 4,798,885 A | 1/1989 | Mason | |
| 4,804,744 A | 2/1989 | Sen | |
| 4,810,691 A | 3/1989 | Seyedin | |
| 4,828,990 A | 5/1989 | Naoki et al. | |
| 4,843,063 A | 6/1989 | Seyedin | |
| 4,851,521 A * | 7/1989 | della Valle et al. | 536/55.1 |
| 4,868,161 A | 9/1989 | Roberts | |
| 4,877,864 A | 10/1989 | Wang et al. | |
| 4,886,747 A | 12/1989 | Derynck | |
| 4,908,204 A | 3/1990 | Robinson et al. | |
| 4,920,962 A | 5/1990 | Proulx | |
| 4,923,805 A | 5/1990 | Reddy et al. | |
| 4,955,892 A | 9/1990 | Daniloff et al. | |
| 4,957,744 A | 9/1990 | della Valle et al. | |
| 4,963,146 A | 10/1990 | Li | |
| 4,968,590 A | 11/1990 | Kuberasampath et al. | |
| 4,992,274 A | 2/1991 | Robinson et al. | |
| 5,011,486 A | 4/1991 | Aebischer et al. | |
| 5,011,691 A | 4/1991 | Oppermann | |
| 5,013,649 A | 5/1991 | Wang et al. | |

(Continued)

FOREIGN PATENT DOCUMENTS

CZ 283073 B6 * 12/1997

(Continued)

OTHER PUBLICATIONS

Kubler et al., Bone morphogenic protein-mediated interaction of periosteum and diaphysis (Sep. 1990) Clinical Osteopaedics and Related Research, No. 258, pp. 279-294.*

(Continued)

*Primary Examiner*—Christopher R. Tate
*Assistant Examiner*—Jennifer Lone Harle
(74) *Attorney, Agent, or Firm*—Finnegan, Henderson, Farabow, Garrett & Dunner, LLP

(57) ABSTRACT

An injectable formulation is disclosed for delivery of osteogenic proteins. The formulation comprises a pharmaceutically acceptable admixture of an osteogenic protein; and formulations comprising osteogenic protein, hyaluronic acid derivatives and tricalcium phosphate are also disclosed. Methods for formulating porous injectable gels and pastes from hyaluronic acid are also disclosed.

29 Claims, 4 Drawing Sheets

U.S. PATENT DOCUMENTS

| | | | |
|---|---|---|---|
| 5,019,087 A | | 5/1991 | Nichols |
| 5,024,841 A | | 6/1991 | Chu et al. |
| 5,026,381 A | | 6/1991 | Li |
| 5,041,538 A | | 8/1991 | Ling et al. |
| 5,071,834 A | | 12/1991 | Burton et al. |
| 5,089,396 A | | 2/1992 | Mason et al. |
| 5,102,807 A | | 4/1992 | Burger et al. |
| 5,106,626 A | | 4/1992 | Parsons et al. |
| 5,106,748 A | | 4/1992 | Wozney et al. |
| 5,108,753 A | | 4/1992 | Kuberasampath |
| 5,108,922 A | | 4/1992 | Wang et al. |
| 5,116,738 A | | 5/1992 | Wang et al. |
| 5,118,667 A | | 6/1992 | Adams et al. |
| 5,124,316 A | | 6/1992 | Antoniades et al. |
| 5,141,905 A | | 8/1992 | Rosen et al. |
| 5,147,399 A | | 9/1992 | Dellon et al. |
| 5,166,058 A | | 11/1992 | Wang et al. |
| 5,166,190 A | | 11/1992 | Mather et al. |
| 5,166,322 A | | 11/1992 | Shaw et al. |
| 5,168,050 A | | 12/1992 | Hammonds |
| 5,171,579 A | | 12/1992 | Ron et al. |
| 5,187,076 A | | 2/1993 | Wozney et al. |
| 5,187,263 A | | 2/1993 | Murray et al. |
| 5,202,120 A | | 4/1993 | Silver et al. |
| 5,206,028 A | | 4/1993 | Li |
| 5,208,219 A | | 5/1993 | Ogawa et al. |
| 5,215,893 A | | 6/1993 | Mason et al. |
| 5,216,126 A | | 6/1993 | Cox et al. |
| 5,217,867 A | | 6/1993 | Evans et al. |
| 5,218,090 A | | 6/1993 | Connors |
| 5,229,495 A | | 7/1993 | Ichijo et al. |
| 5,256,418 A | | 10/1993 | Kemp et al. |
| 5,258,494 A | | 11/1993 | Oppermann et al. |
| 5,266,683 A | | 11/1993 | Oppermann et al. |
| 5,278,145 A | | 1/1994 | Keller et al. |
| 5,284,756 A | | 2/1994 | Grinna et al. |
| 5,286,654 A | | 2/1994 | Cox et al. |
| 5,290,271 A | * | 3/1994 | Jernberg |
| 5,292,802 A | | 3/1994 | Rhee et al. |
| 5,306,307 A | | 4/1994 | Senter et al. |
| 5,308,889 A | | 5/1994 | Rhee et al. |
| 5,324,519 A | | 6/1994 | Dunn et al. |
| 5,324,775 A | * | 6/1994 | Rhee et al. |
| 5,328,955 A | | 7/1994 | Rhee et al. |
| 5,336,767 A | | 8/1994 | della Valle et al. |
| 5,352,715 A | | 10/1994 | McMullin et al. |
| 5,354,557 A | | 10/1994 | Oppermann et al. |
| 5,356,629 A | * | 10/1994 | Sander et al. |
| 5,364,839 A | | 11/1994 | Gerhart et al. |
| 5,366,875 A | | 11/1994 | Wozney et al. |
| 5,399,346 A | | 3/1995 | Anderson et al. |
| 5,399,677 A | | 3/1995 | Wolfman et al. |
| 5,405,390 A | | 4/1995 | O'Leary et al. |
| 5,411,941 A | | 5/1995 | Grinna et al. |
| 5,413,989 A | * | 5/1995 | Ogawa et al. |
| 5,420,243 A | | 5/1995 | Ogawa et al. |
| 5,422,340 A | | 6/1995 | Ammann et al. |
| 5,447,725 A | | 9/1995 | Damiani et al. |
| 5,455,041 A | | 10/1995 | Genco et al. |
| 5,455,329 A | | 10/1995 | Wingender |
| 5,457,047 A | | 10/1995 | Wingender |
| 5,457,092 A | | 10/1995 | Schluter |
| 5,459,047 A | | 10/1995 | Wozney et al. |
| 5,464,440 A | * | 11/1995 | Johansson |
| 5,508,263 A | | 4/1996 | Grinna et al. |
| 5,516,654 A | | 5/1996 | Israel |
| 5,520,923 A | | 5/1996 | Tjia et al. |
| 5,525,148 A | * | 6/1996 | Chow et al. ........ 106/35 |
| 5,538,892 A | | 7/1996 | Donahoe et al. |
| 5,540,121 A | | 7/1996 | Helmers |
| 5,543,394 A | | 8/1996 | Wozney et al. |
| 5,545,616 A | | 8/1996 | Woddruff |
| 5,547,854 A | | 8/1996 | Donahoe et al. |
| 5,556,767 A | | 9/1996 | Rosen et al. |
| 5,618,924 A | | 4/1997 | Wang et al. |
| 5,631,142 A | | 5/1997 | Wang et al. |
| 5,635,372 A | | 6/1997 | Celeste et al. |
| 5,635,373 A | | 6/1997 | Wozney et al. |
| 5,637,480 A | | 6/1997 | Celeste et al. |
| 5,639,638 A | | 6/1997 | Wozney et al. |
| 5,645,592 A | * | 7/1997 | Nicolais et al. |
| 5,648,467 A | | 7/1997 | Kobayashi et al. |
| 5,650,494 A | | 7/1997 | Cerletti et al. |
| 5,658,882 A | | 8/1997 | Celeste et al. |
| 5,661,007 A | | 8/1997 | Wozney et al. |
| 5,674,292 A | | 10/1997 | Tucker et al. |
| 5,688,678 A | | 11/1997 | Hewick et al. |
| 5,693,779 A | | 12/1997 | Moos, Jr. et al. |
| 5,700,664 A | | 12/1997 | Bennett et al. |
| 5,700,774 A | | 12/1997 | Hattersley et al. |
| 5,700,911 A | | 12/1997 | Wozney et al. |
| 5,703,043 A | | 12/1997 | Celeste et al. |
| 5,728,679 A | | 3/1998 | Celeste et al. |
| 5,750,651 A | | 5/1998 | Oppermann et al. |
| 5,752,974 A | * | 5/1998 | Rhee et al. |
| 5,756,457 A | | 5/1998 | Wang et al. |
| 5,786,217 A | | 7/1998 | Tubo et al. |
| 5,813,411 A | * | 9/1998 | Van Bladel et al. ........ 128/898 |
| 5,827,733 A | | 10/1998 | Lee et al. |
| 5,846,931 A | | 12/1998 | Hattersley et al. |
| 5,849,880 A | | 12/1998 | Wozney et al. |
| 5,866,364 A | | 2/1999 | Israel et al. |
| 5,932,216 A | | 8/1999 | Celeste et al. |
| 5,935,594 A | * | 8/1999 | Ringeisen et al. |
| 5,936,067 A | | 8/1999 | Graham et al. |
| 5,939,323 A | * | 8/1999 | Valentini et al. |
| 5,939,388 A | | 8/1999 | Rosen et al. |
| 5,942,499 A | | 8/1999 | Radomsky |
| 5,965,403 A | | 10/1999 | Celeste et al. |
| 5,972,368 A | | 10/1999 | MacKay |
| 5,986,058 A | | 11/1999 | Lee et al. |
| 6,001,352 A | | 12/1999 | Boyan et al. |
| 6,004,937 A | | 12/1999 | Wood et al. |
| 6,027,919 A | | 2/2000 | Celeste et al. |
| 6,034,061 A | | 3/2000 | Rosen et al. |
| 6,034,062 A | | 3/2000 | Thies et al. |
| 6,132,214 A | * | 10/2000 | Suhonen et al. |
| 6,150,328 A | | 11/2000 | Wang et al. |
| 6,177,406 B1 | | 1/2001 | Wang et al. |
| 6,187,742 B1 | * | 2/2001 | Wozney et al. |
| 6,190,880 B1 | | 2/2001 | Israel et al. |
| 6,207,813 B1 | | 3/2001 | Wozney et al. |
| 6,245,889 B1 | | 6/2001 | Wang et al. |
| 6,284,872 B1 | | 9/2001 | Celeste et al. |
| 6,287,816 B1 | | 9/2001 | Rosen et al. |
| 6,291,206 B1 | | 9/2001 | Wozney et al. |
| 6,331,612 B1 | | 12/2001 | Celeste et al. |
| 6,340,668 B1 | | 1/2002 | Celeste et al. |
| 6,432,919 B1 | | 8/2002 | Wang et al. |
| 6,437,111 B1 | | 8/2002 | Wozney et al. |
| 6,558,925 B2 | | 5/2003 | Graham et al. |
| 6,586,388 B2 | | 7/2003 | Oppermann et al. |
| 6,593,109 B1 | | 7/2003 | Israel et al. |
| 6,599,516 B1 | * | 7/2003 | Knaack ........ 424/423 |
| 6,610,513 B2 | | 8/2003 | Wozney et al. |
| 6,613,744 B2 | | 9/2003 | Wozney et al. |
| 6,623,934 B2 | | 9/2003 | Celeste et al. |
| 6,670,293 B2 | * | 12/2003 | Edwards et al. ........ 501/84 |
| 6,699,471 B2 | * | 3/2004 | Radice et al. ........ 424/93.7 |

| | | | | | | |
|---|---|---|---|---|---|---|
| | 6,709,678 B2 * | 3/2004 | Gruber ............... 424/490 | WO | WO 93/16099 | 8/1993 |
| | 6,719,968 B2 | 4/2004 | Celeste et al. | WO | WO 93/19177 | 9/1993 |
| | | | | WO | WO 93/20858 | 10/1993 |
| | FOREIGN PATENT DOCUMENTS | | | WO | WO-9320858 A1 * | 10/1993 |
| EP | 0 052 510 | 5/1982 | | WO | WO 94/01557 | 1/1994 |
| EP | 0 058 481 | 8/1982 | | WO | WO 94/03200 | 2/1994 |
| EP | 0 121 976 | 10/1984 | | WO | WO 94/06449 | 3/1994 |
| EP | 0 128 041 | 12/1984 | | WO | WO 94/11502 | 5/1994 |
| EP | 0 148 155 | 7/1985 | | WO | WO 94/15949 | 7/1994 |
| EP | 0 155476 | 9/1985 | | WO | WO 94/15965 | 7/1994 |
| EP | 0 169 016 | 1/1986 | | WO | WO 94/15966 | 7/1994 |
| EP | 0 177 343 | 4/1986 | | WO | WO 94/21681 | 9/1994 |
| EP | 0 222 491 | 10/1986 | | WO | WO 94/24285 | 10/1994 |
| EP | 0 212 474 | 3/1987 | | WO | WO 94/26892 | 11/1994 |
| EP | 0 329 239 | 8/1989 | | WO | WO 94/26893 | 11/1994 |
| EP | 0 401 055 | 12/1990 | | WO | WO 95/01801 | 1/1995 |
| EP | 0 409 472 | 1/1991 | | WO | WO 95/01802 | 1/1995 |
| EP | 0 416 578 | 3/1991 | | WO | WO 95/05846 | 3/1995 |
| EP | 0 429 570 | 6/1991 | | WO | WO 95/07982 | 3/1995 |
| EP | 0 433 225 | 6/1991 | | WO | WO 95/10539 | 4/1995 |
| EP | 0 512 844 | 11/1992 | | WO | WO 95/10611 | 4/1995 |
| EP | 0 530 804 | 3/1993 | | WO | WO 95/12664 | 5/1995 |
| EP | 0 531 448 | 11/1994 | | WO | WO 95/15966 | 6/1995 |
| EP | 0 626 451 | 11/1994 | | WO | WO 95/16035 | 6/1995 |
| EP | 0 688 869 | 12/1995 | | WO | WO 95/33830 | 12/1995 |
| EP | 0 831 884 | 5/1996 | | WO | WO 96/01845 | 1/1996 |
| EP | 0 313 578 | 8/1996 | | WO | WO 96/02559 | 2/1996 |
| EP | 0 741 187 | 11/1996 | | WO | WO 96/36710 | 11/1996 |
| EP | 0 592 562 | 1/1999 | | WO | WO 96/38570 | 12/1996 |
| EP | 1 061 940 | 2/1999 | | WO | WO 96/39170 | 12/1996 |
| EP | 0 536 186 | 11/2001 | | WO | WO 96/39203 | 12/1996 |
| JP | 05-123390 A2 | 5/1993 | | WO | WO 96/40883 | 12/1996 |
| JP | 03-345189 | 7/1993 | | WO | WO 97/15321 | 5/1997 |
| JP | 05-277174 A2 | 10/1993 | | WO | WO 97/22308 | 6/1997 |
| WO | WO 84/01106 | 3/1984 | | WO | WO97/49412 | 6/1997 |
| WO | WO 85/04173 | 9/1985 | | WO | WO-9722308 A1 * | 6/1997 |
| WO | WO 86/00525 | 1/1986 | | WO | WO97/32591 | 9/1997 |
| WO | WO 86/00639 | 1/1986 | | WO | WO 97/34626 | 9/1997 |
| WO | WO 87/00528 | 1/1987 | | WO | WO 97/40137 | 10/1997 |
| WO | WO 88/00205 | 1/1988 | | WO | WO 97/45532 | 12/1997 |
| WO | WO 89/09787 | 10/1989 | | WO | WO 97/48275 | 12/1997 |
| WO | WO 89/09788 | 10/1989 | | WO | WO 97/49412 | 12/1997 |
| WO | WO 89/10133 | 11/1989 | | WO | WO 98/16641 | 4/1998 |
| WO | WO 89/10409 | 11/1989 | | WO | WO 98/31788 | 7/1998 |
| WO | WO 90/03733 | 4/1990 | | WO | WO 98/34951 | 8/1998 |
| WO | WO 90/11366 | 10/1990 | | WO | WO 98/40113 | 9/1998 |
| WO | WO 91/02744 | 3/1991 | | WO | WO 98/49296 | 11/1998 |
| WO | WO 91/04274 | 4/1991 | | WO | WO99/24070 | 11/1998 |
| WO | WO 91/05802 | 5/1991 | | WO | WO 99/01159 | 1/1999 |
| WO | WO91/17777 | 5/1991 | | WO | WO 99/24070 | 5/1999 |
| WO | WO 91/10444 | 7/1991 | | WO | WO 99/31120 | 6/1999 |
| WO | WO 91/17777 | 11/1991 | | WO | WO 99/37320 | 7/1999 |
| WO | WO 91/18047 | 11/1991 | | WO | WO 99/38543 | 8/1999 |
| WO | WO 91/18098 | 11/1991 | | WO | WO 99/45949 | 9/1999 |
| WO | WO 92/05198 | 4/1992 | | WO | WO00/37124 | 12/1999 |
| WO | WO 92/05199 | 4/1992 | | WO | WO 00/37124 | 6/2000 |
| WO | WO 92/07004 | 4/1992 | | WO | WO 00/43781 A | 7/2000 |
| WO | WO 92/07073 | 4/1992 | | WO | WO 2003099992 A2 * | 12/2003 |
| WO | WO 92/14481 | 9/1992 | | | | |
| WO | WO 92/15323 | 9/1992 | | | | |
| WO | WO 92/09697 | 11/1992 | | | OTHER PUBLICATIONS | |
| WO | WO 92/20793 | 11/1992 | | | | |
| WO | WO 92/22319 | 12/1992 | | | | |
| WO | WO 93/00049 | 1/1993 | | | | |
| WO | WO 93/00050 | 1/1993 | | | | |
| WO | WO 93/00432 | 1/1993 | | | | |
| WO | WO 93/04692 | 3/1993 | | | | |
| WO | WO 93/05751 | 4/1993 | | | | |
| WO | WO 93/09228 | 5/1993 | | | | |
| WO | WO 93/09229 | 5/1993 | | | | |
| WO | WO 93/09802 | 5/1993 | | | | |
| WO | WO 93/13206 | 7/1993 | | | | |

Urist et al., "β-Tricalcium Phosphate Delivery System for Bone Morphogenetic Protein" (1984) Clin. Orthoped. Rel. Res., 187, 277-280.*

Urist et al., "Bone Regeneration Under the Influence of a Bone Morphgenetic Protein (BMP) β-Tricalcium Phosphate (TCP) Composite in Skull Trephine Defects in Dogs" (1986) (Clin. Orthoped. Rel. Res., 214, 295-304.*

Uhura et al., "Resorption of, and Bone Formation from, New β-Tricalcium Phosphate-Monocalcium Phosphate Cements: An in vivo Study" (1996) J. Biomed. Mat. Res., 30, 193-200.*

Uhura et al., "Healing of Segmental Bone Defects in Rats Induced by a β-TYCP-MCPM Cement Combined with rhBMP-2" (1999) J. Biomed. Mat. Res., 44, 168-175.*
Campoccia et al., "Semisynthetic Resorbable Materials from Hyaluronan Esterification" (Dec. 1988) Biomaterials, 19(23), 2101-2127.*
Aiba et al., Blood, 90:3923-3030 (1997).
Alberts et al., Molecular Biology of the Cell, Third Ed., Garland Publishing, Inc., New York, NY, pp. 1142 (1983)—1145, 1151, 1161 & 1162.
Amizuka et al., J. Cell Biol., 126:1611-1623 (1994).
Attisano et al., Cell, 68:97-108 (1992).
Baird et al., Biochem. Biophys. Res. Comm., 138:476-482 (1986).
Barres. B.A. et al., Development, 118:283-295 (1993).
Basler, K. et al., Cell, 73:687-702 (1993).
Beck et al., Growth Factors, 2:273-282 (1990).
Belo et al., Mech. Devel., 68:45-57 (1997).
Bendig, Genetic Engineering, 7:91-127 (1988).
Biben et al., Develop. Biol., 194:135-151 (1998).
Bignami et al., Brain Res., 43:429-435 (1972).
Bignami, A. et al., Plasticity and Regeneration of the Nervous System, 197-206 (1991).
Bolton et al., Biochem J., 133:529 (1973).
Border et al., J. Clin. Invest., 90:1-7 (1992).
Bouwmeester et al., Nature, 382:595-601 (1996).
Bowen-Pope et al., J. Biol. Chem., 237:5161 (1982).
Bowie et al., Science, 247:1306-1310 (1990).
Brown et al., J. Immunol., 142:679 (1989).
Broxmeyer et al., PNAS, 85:9052 (1988).
Bruder et al., J. Cell Biochem., 56:283-294 (1994).
Burt, D.W., BBRC, 184:590-595 (1992).
Campoccia et al., Biomaterials, 19:2101-27 (1998).
Caplan, A., Bone Repair and Regeneration, 21:429-435 (1994).
Celeste et al., J. Bone Mineral Res., 9:suppl. 5136 (1994).
Celeste et al., PNAS, 87:9843-9847 (1990).
Chang et al., J. Biol. Chem., 269:28227-28234 (1994).
Conlon et al., Development, 120:1919 (1994).
Conlon et al., Development, 111:969 (1991).
Collignon et al., Nature, 381:155 (1996).
Creighton, T.E., Proteins: Structure and Molecular Principles, W.H. Freeman and Co., New York (1982) (Table of Contents only).
Cunningham et al., PNAS, 89:11740-11744 (1992).
Dagert et al., Gene, 6:23 (1979).
Dale et al., EMBO J., 12:4471 (1993).
D'Alessandro et al., Growth Factors, 11:53-69 (1994).
D'Allesandro et al., J. Bone Mineral Res., (6) Suppl: 1:S153 (1991).
DeWulf et al., Endocrinology, 136:2652-2663 (1995).
Dexter et al., Nature, 344:380 (1990).
DiLeone et al., Genetics, 148:401-408 (1998).
Doctor et al., Dev. Biol., 151:591-605 (1992).
Ducy et al., Kidney Intl., 57:2207-2214 (2000).
Dunn et al., Cancer Cells, 3:227-234 (1985).
Ebner et al., Science, 260:1344-1348 (1993).
Estevez et al., Nature, 365:644-649 (1993).
Eto et al., Biochem. Biophys. Res. Comm., 142:1095 (1987).
Fainsod et al., Mech. Dev., 1:39-50 (1997).
Fallon et al., J. Cell Biol., 100:198-207 (1985).
Fenton et al., Endocrinology, 129:1762-1768 (1991).
Finch et al., PNAS, 94:6770-6775 (1997).
Frishchauf et al., J. Mol. Biol., 170:827-842 (1983).
Frommel et al., J. Mol. Evol., 24:233-257 (1985.
Gamer et al., Develop. Biol., 208:222-232 (1999).
Geisert et al., Develop. Biol., 143:335-345 (1991).
Gerhart et al., Trans. Othop. Res. Soc., 16:172 (1991).
Gething et al., Nature, 293:620-625 (1981).
Gitelman et al., J. Cell. Biol., 126:1595-1609 (1994).
Goodman, R., Methods for Serum-Free Culture of Neuronal and Lymphoid Cells, 23-36 (1984).
Gough et al., EMBO J., 4:645-653 (1985).
Graham et al., EMBO, 15:6505-6515 (1996).
Graham et al., Growth Factors, 7:151-160 (1992).
Graham et al., J. Biol. Chem., 269:4974-4978 (1994).
Graham et al., Nature, 344:442 (1990)—444.

Guignon et al., Chem. Abstracts, 96:36, Abstract No. 115633h (1982).
Guignon et al., Cancer Res., 42:638 (1982).
Hammonds et al., Mol. Endocrin., 5:149-155 (1991).
Harrison et al., Exp. Cell Res., 92:340-345 (1991).
Hasimoto et al., J. Biol. Chem., 267:7203-7206 (1992).
He et al., Develop. Dynamics, 196:133-142 (1993).
Hebda et al., J. Invest. Dermatol., 91:440-445 (1988).
Hefti et al., J. Neurobiol., 25:1418-1435 (1994).
Hemmati-Brinvanlou et al., Nature, 359:609-614 (1992).
Hoang et al., J. Biol. Chem., 271:26131-26137 (1996).
Hollnagel et al., Calcified Tissue Int'l, 56:430 (1995).
Hunkapiller et al., Meth. Enzymol., 91:399-413 (1983).
Inouye et al., Mol. Cell. Endocrinol., 90:1 (1992)-6.
Iwasaki, J. Biol. Chem., 271:17360-5 (1996).
Janowska-Wieczorek et al., Biol. Abstracts, Reviews-Reports-Meetings, 33:61402 (1987).
Jonhagen et al., Dement. Cogn. Disord., 9:246-257 (1998).
Joyce et al, J. Cell Biochem., Suppl.17E:136, Abstract R504 (1993).
Kalyani et al., J. Neuroscience, 18:7856-7869 (1998).
Karaplis et al., Mol. Endocrin., 4:441-446 (1990).
Karaplis et al., Genes & Development, 8:277-289 (1994).
Katagiri et al., J. Cell Biol., 127:1755-1766 (1994).
Kaufman et al., Mol. Cell Biol., 2:1304-1319 (1982).
Kaufman et al., Mol. Cell Biol., 5:1750-1759 (1985).
Kaufman et al., J. Mol. Biol., 159:601-629 (1982).
Kaufman et al., PNAS, 82:689-693 (1985).
Kingsley et al., Cell, 71:399-410 (1992).
Kingsley et al., Genes & Development, 8:133-146 (1994).
Klein-Nulend et al., Tissue Engineering, 4:305-313 (1998).
Klein et al., Brain Res. 875:144-151 (2000).
Kliot et al., Exper. Neur., 109:57-69 (1990).
Koenig et al., Mol. Cell Biol., 14:5961-5974 (1994).
Koopman et al., JBC, 273:10103-10109 (1997).
Krueger, G.G., , N. E. J. Med., 328:1845-1846 (1993).
LaPan et al., Program and Abstract, 13th Ann. Mtg of the AM Society of Bone and Min. Res., Aug. 24-28, p. 5153, Abstract No. 280, Mary Ann Liebert, Inc. NY (1991).
Lathe, J., J. Mol. Biol., 183:1-12 (1985).
Lawn et al., Cell, 15:1157-1174 (1978).
Lefer et al., PNAS, 90:1018-22 (1993.
LeMaire et al., Trends in Genetics, 12:525-531 (1996).
Leslie M., Nurse Practitioner, 24:38, 41-8 (1999).
Lewin, Science, 237:1570 (1987).
Leyns et al., Cell, 88:747-756 (1997).
Lin et al., Cell, 68:775-785 (1992).
Lin et al., Science, 260:1130-1132 (1993).
Lipes et al., PNAS, 85:9704 (1988).
Lodish et al., Mol. Cell Biol., 3rd Ed., W.H. Freeman & Co., p266 (1995).
Lopez-Coviella et al., J. Physiol. Paris., 92:460-461 (1998).
Lopez-Coviella et al., Science, 289:313-316 (2000).
Lopez-Coviella et al., Xth International Symposium on Cholinergic Mechanisms (1998), pp. 409-410, 460-461.
Lopez-Coviella et al., Soc. Neurosci. Abstracts, 25:517 (1999).
Lord et al., Brit. J. Haematol., 34:441 (1976)—445.
Lorimore et al., Leuk. Res., 14:481-489 (1990).
Lowe et al., Nature, 381:158 (1996)—161.
Lucas et al., Differentiation, 37:47-52 (1988).
Luthman et al., Nucl. Acids Res., 11:1295-1308 (1983).
Luyten et al., J. Biol. Chem., 264:13377-13380 (1989).
Luyten et al., Exp. Cell. Res., 210(2):224-229 (1994).
Lyons et al., PNAS, 86:4554-4558 (1989).
Mangin et al., PNAS, 85:597-601 (1988).
Mangin et al., Gene, 95:195-202 (1990).
Maniatis et al., Mol. Cloning, A Laboratory Manual, Cold Spring Harbor Laboratory, CSH., N.Y.:310-323, 387-389 & 404-433 (1982).
Mantel et al., PNAS, 90:2232-2236 (1993).
Mansour et al., J. Neurosci. Res., 25:300-377 (1990).
Marieb, E.N., In Human Anatomy and Physiology, 2nd Ed., The Benjamin/Cummings Publishing Co., pp. 373-375 (1992).
Mark, J. Cell. Biol., 130:701-10 (1995).

Marra et al., *EMBL Database*, Accession No. AA120122 (1996).
Martin et al., *Crit. Rev. Biochem. Mol. Biol.*, 26:377-395 (1991).
Mason et al., *Nature*, 318:659-663 (1985).
Massague et al., *Trends in Cell Biol.*, 4:172-178 (1994).
Massague et al., *Cell*, 69:1067-1070 (1992).
Massague et al., *Cell*, 49:437-438 (1987).
Mathews et al., *Cell*, 65:973-982 (1991).
Matsuzaki et al., *J. Biol. Chem.*, 268:12719-12723 (1993).
Matzuk et al., *Nature*, 360:313 (1992)—319.
McConahey et al., *Int. Arch. Allergy*, 29:185-189 (1966).
McDonald et al., *Cell*, 73:421-424 (1993).
Miller et al., *J. Immunol.*, 143:2907 (1989)-2916.
Miller et al., *Genetic Engineering*, 8:277-298 (1986).
Miyazono et al., *Gen Bank Record No. Z23154* (1993).
Morii et al., *J. Biol. Chem.*, 258:12749-12752 (1983).
Mullins et al., *Nature*, 303:856-858 (1984).
Nabeshima et al., *Alz Dis. And Assoc. Disord. 14(Suppl. 1)*:S39-S46 (2000).
Nakamura et al., *J. Biol. Chem.*, 267:18924-18928 (1992).
Nakao et al., *Mol. Cell Biol.*, 10:3646-3658 (1990).
Nakatani T., *Jap. J. Clin. Med.*, 52:824-33 (1994) (Abstract Only).
Nathan et al., *J. Cell Biol.*, 113:981-986 (1991).
Neuhaus et al., *Mech. Dev.*, 80:181-184 (1999).
Nirschl, R., *American Orthopaedic Society for Sports Medicine*, Leadbetter, W. et al., eds, Ch. 13:577-585 (1989).
Ngo et al., Merz et al., eds., Brickhauser, Boston, Springer-Verlag, pp 433-434 & 492-495 (1994).
Noble et al., *J. Neuroscience*, 4:1892-1903 (1984).
Obaru et al., *J. Biochem.*, 99:885 (1986)-894.
Ogawa et al., *J. Biol. Chem.*, 267:14233 (1992)—14237.
Ohura et al., *J. Biomed. Mat. Res.*, 30:193-200 (1996).
Ohura et al., *J. Biomed. Mat. Res.*, 44: 168-175 (1999).
Okayama et al., *Mol. Cell Biol.*, 2:161-170 (1982).
Ozkaynak et al., *EMBO Journal*, 9:2085-2093 (1990).
Padgett et al., *Nature*, 325:81-84 (1987).
Paralkar, et al., *J. Cell Biol.*, 119:1721-1728 (1992).
Park et al., *J. Biol. Chem.*, 271:8161-9 (1996).
Patel et al., Pharmacotherapy of Cognitive Impairment in Alzheimer's Disease: A Review:81-95 (1992).
Perides et al., *J. Biol. Chem.*, 269:765-770 (1994).
Perides et al., *PNAS*, 89:10326-10330 (1992).
Peyron, J.G. *J. Rheumatol. Suppl.*, 27:2-3 (1991).
Pierce et al., *J. Clin. Investig.*, 96:1336-50 (1995).
Pollock, *J. Biol. Chem.*, 271:8008-14 (1996).
Pragnell et al., *Blood*, 72:196-201 (1988).
2001-2002 Progress Report on Alzheimer's Disease, *National Institute on Aging; NIH*:1-51 (2002).
Rabin et al., *Mol. Cell. Biol.*, 13:2203-2213 (1993).
Ralph et al., *Cancer Res.*, 37:546 (1977).
Ralph et al., *J. Immunol.*, 114:898 (1975).
Rattner et al., *PNAS*, 94:2859-2863 (1997).
Reddi, A. *JBJS*, 83-A:S1-1:S1-S6 (2001).
Reddi et al., *Osteoporosis*, Academic Press, pp. 281-287 (1996).
Reddi et al., *PNAS*, 69:1601 (1972).
Reeck, *Cell*, 50:667 (1987).
Roberts et al., *PNAS*, 83:4167-4171 (1986).
Robertson et al., *Biochem. Biophys. Res. Commun.*, 149:744-749 (1987).
Rodeo et al., *Orthopaedic Res. Soc.*, 41st Annual Mtg, Orlando, Florida, p. 288 (1995).
Rodeo, et al., *J. Bone Joint Surg.*, 75-A:1795-1803 (1993).
Rosen et al., *Trends in Genetics*, 8:97-102 (1992).
Rosen et al., *Connect Tissue Res.*, 20:313-9 (1989).
Rubin et al., *Science*, 287:2204-2215 (2000).
Rudinger, *Peptide Hormones*, Parsons (ed.), U Park Press, Baltimore:1-7 (1976).
Sakai et al., *PNAS*, 87:8378-8382 (1990).
Salic et al., *Development*, 124:4739-4748 (1997).
Sambrook et al., *Mol. Cloning: A Laboratory Manual, $s^{nd}$ Ed.*, vols. 1, 2 and 3, Cold Spring Harbor Laboratory Press: Cold Spring Harbor, New York, USA (1989) (Table of Contents Only).
Sampath et al., *J. Biol Chem.*, 267:20352-20362 (1992).
Sampath et al., *J. Biol Chem.*, 265:13198-13205 (1990).
Sampath et al., *PNAS*, 84:7109-7113 (1987).
Sampath et al., *PNAS*, 80:6591-6595 (1983).
Sampath et al., *Exp. Cell. Res.*, 143:460-64 (1982).
Sato et al., *Clin. Orthopaedics Related Res.*, 183:180-187 (1984).
Saukkonon et al., *J. Exp. Med.*, 171:439 (1990).
Schubert et al., *Nature*, 344:868-870 (1990).
Schulz et al., *Principles of Protein Structure*, Springer-Verlag New York, Inc., New York:14-16 (1979).
Shah, et al., *J. Cell Sci.*, 108:985-1002 (1995).
Shimasaki et al., *PNAS*, 85:4218-4222 (1988).
Shipley et al., *Cancer Res.*, 46:2068-2071 (1986).
Shoda et al., *Growth Factors*, 8:165-172 (1993.
Smith et al., *Brain Res.*, 543:111-122 (1991).
Smith et al., *Dev. Biol.*, 138:377-390 (1990).
Smith et al., *J. Neurochem.*, 60:1453-1466 (1993).
Sompayrac et al., *PNAS*, 78:7575-7578 (1981).
Song et al., *Mol. Biol. Cell*, 5:384a (1994) and 34th Ann. Mtg of the American Soc. for Cell Biol., San Francisco, CA (1994).
Sporn et al., *Nature*, 332:217-219 (1988).
Sporn et al., *Science*, 233:532-534 (1986).
Storm et al., *Nature*, 368:639-642 (1994).
Sugino et al., *J. Biol. Chem.*, 268:15579 (1993).
Suggs et al., *PNAS*, 78:6613-6617 (1981).
Sumitomo et al., *Biochem. Biophys. Acta.*, 208:1 (1995).
Sumitomo et al., *DNA Sequence-J. DNA Sequence and Mapping* 3:297-302 (1993).
Suzuki et al., *Proc. Natl Acad Sci USA* 91:10255-59 (1994).
Tabas et al., *Genomics*, 9:283-289 (1991).
Takagi et al., *Clin. Orthopaed. Related Res.*, 171:224-231 (1982).
Taniguchi et al., *PNAS*, 77:5230-5233 (1980).
Tatusova et al., *FEMS Microbiol. Lett.*, 174:247-250 (1990).
Ten Dijke et al., *J. Biol. Chem.*, 269:16985-16988 (1994).
Ten Dijke et al., *EMBL Z22534* (Apr. 6, 1993).
Ten Dijke et al., *EMBL Sequence Database, European Molecular Biology Laboratory (Basel, CH)*, Accession No. Z22535 (1993).
Ten Dijke et al., *EMBL Sequence Database, European Molecular Biology Laboratory (Basel, CH)*, Accession No. Z22536 (1993).
Thies et al., *J. Bone Min. Res.*, 5:305 (1990).
Thies et al., *Endocrinol.*, 130:1318-1324 (1992).
Thomsen et al., *Trends in Genetics*, 13:209-211 (1997).
Thomsen et al., *Cell*, 74:433-441 (1993).
Tona et al., *J. Histochem. Cytochem.*, 41:591-599 (1993).
Toriumi et al., *Arch. Otolaryngol. Head Neck Surg.*, 117:1101-1112 (1991).
Tsuchida et al., *PNAS*, 90:11242-11246 (1993).
Tsukazaki et al., *Calcif. Tissue Int.*, 57:196-200 (1995).
Tuszynski, *Cell Transplantation*, 9:629-636 (2000).
Ueno et al., *PNAS*, 84:8282-8286 (1987).
Ulrich et al., *EMBO J.*, 3:361-364 (1984).
Urdal et al., *PNAS*, 81:6481-6485 (1984).
Urist et al., *Fed. Proceed.*, Bethesda, MD, US, 3:746 (1985).
Urist et al., *PNAS*, 81:371-375 (1984).
Urist et al., *Clin. Orthopaed. and Related Res.*, 187: 277-280 (1984).
Urist et al., *Proc. Soc. Exper. Biol. & Med.*, 2:194 (1983).
Urist et al., *Science*, 220:680-686 (1983).
Urist et al., *PNAS*, 70:3511 (1973).
Urist et al., *Clin. Orthoped. Rel. Res.*, 214:295-304 (1986).
Urlaub et al., *PNAS*, 77:4216-20 (1980).
Vukicevic et al. *PNAS*, 93:9021-6 (1996).
Wall et al., *J. Cell Biol.*, 120:493-502 (1993).
Wang et al., *Cell*, 67:797-805 (1991).
Wang et al., *J. Cell Biochem.*, Suppl. 15, Part E, p. 161, Abstract Q020 (1991).
Wang et al., *PNAS*, 87:2220-2224 (1990).
Wang et al., *PNAS*, 85:9484-9488 (1988).
Wang, E.A., *Trends in Biotech.*, 11:379-383 (1993).
Wang et al., *Cell*, 88:757-766 (1997).
Wang et al., *Stroke*, 32:2170-2178 (2001).
Weeks et al., *Cell*, 51:861-867 (1987).
Wells, *Biochemistry*, 29:8509-8517 (1990).
Wharton et al., *PNAS*, 88:9214-9218 (1991).
Wolpe et al., *FASEB J.*, 3:2565-2573 (1989).

Wolpe et al., *J. Biochem. Suppl. O*, Abstract H141, 13 Part C:21 (1989).
Wolpe et al., *J. Exp. Med.*, 167:570 (1988).
Wong et al., *Science*, 228:810-815 (1985).
Woo et al., *PNAS*, 75:3688-3691 (1978).
Wood et al., *PNAS*, 82:1585-1588 (1985).
Wozney et al., *J. Cell Sci.*, Suppl. 13:149-156 (1990).
Wozney, *Mol. Reproduction & Develop.*, 32:160-167 (1992).
Wozney et al., *Science*, 242:1528-1534 (1988).
Wozney, J.M., *Prog. Growth Factor Res.*, 1:267-280 (1989).
Wozney et al., *Handbook of Exp. Pharm.*, eds., G.R. Mundy and T.J. Martin; Springer-Verlag, Berlin, Chapter 20, 107:725-748 (1993).
Wozney, *Cell. & Mol. Biol. Bone*, pp. 131-167 (1993) (Academic Press, Inc.).
Wozney et al., *J. Cell Biochem.*, Suppl. 16F:76 Abstract (1992).
Wozney *Spine*, 27:S2-S8 (2002).
Wright et al., *Leukemia Res.*, 4:537 (1980).
Wright et al., *Cell Tissue Kinet.*, 18:193 (1985).

Xu et al., *Proc Natl Acad Sci USA*, 91:7957-61 (1994).
Yamaguchi et al., *Nippon Rinsho*, 50:1932-1938 (1992).
Yamaji et al., *Biochem. Biophys. Res. Comm.*, 205:1944-1951 (1994).
Zipfel et al., *J. Immunol.*, 142:1582 (1989).
Zheng et al., *Path. Res. Pract.*, 188:1104-1121 (1992).
Zhou et al., *Nature*, 361:543-547 (1993).
Brun, et al. "Chondrocyte aggregation and reorganization into three-dimensional scaffolds," *Biomedical Materials Research*, 46(3): 337-346 (1999).
Copy of Notice of Opposition to a European Patent for 1 223 990 B1 dated Apr. 28, 2005.
Vercruysse, et al., "Hyaluronate Derivatives in Drug Delivery," *Critical Reviews in Therapeutic Drug Carrier Systems*, 15(5): 513-555 (1998).

\* cited by examiner

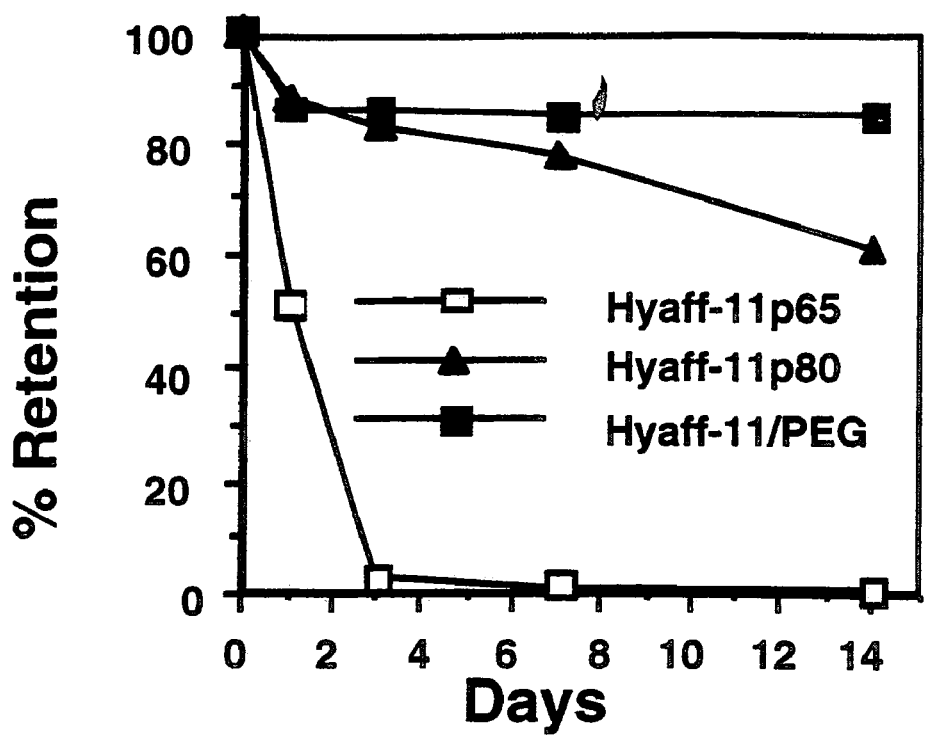
Figure 1: In vitro release kinetics of $^{125}$I-rhBMP-2 in gels of Hyaff-11/PEG, Hyaff-11p80, Hyaff-11p65.

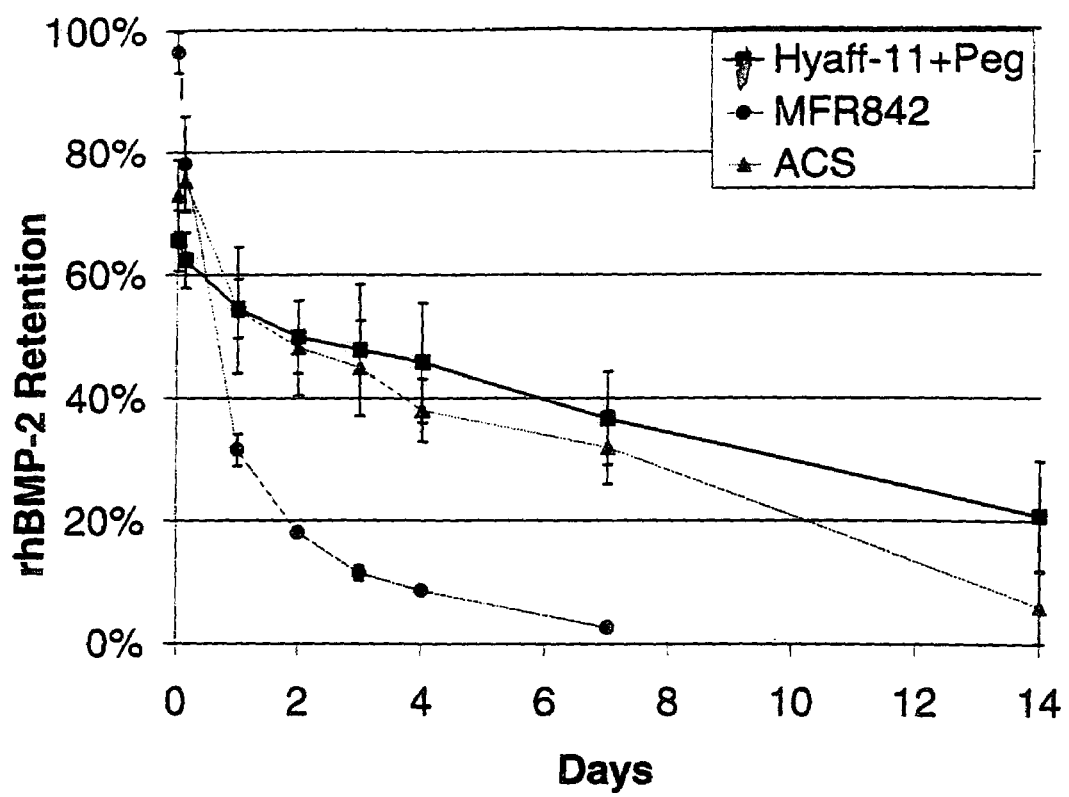
Figure 2: In vivo retention of $^{125}$I-rhBMP-2 in Hyaff-11/PEG, ACS, and buffer.

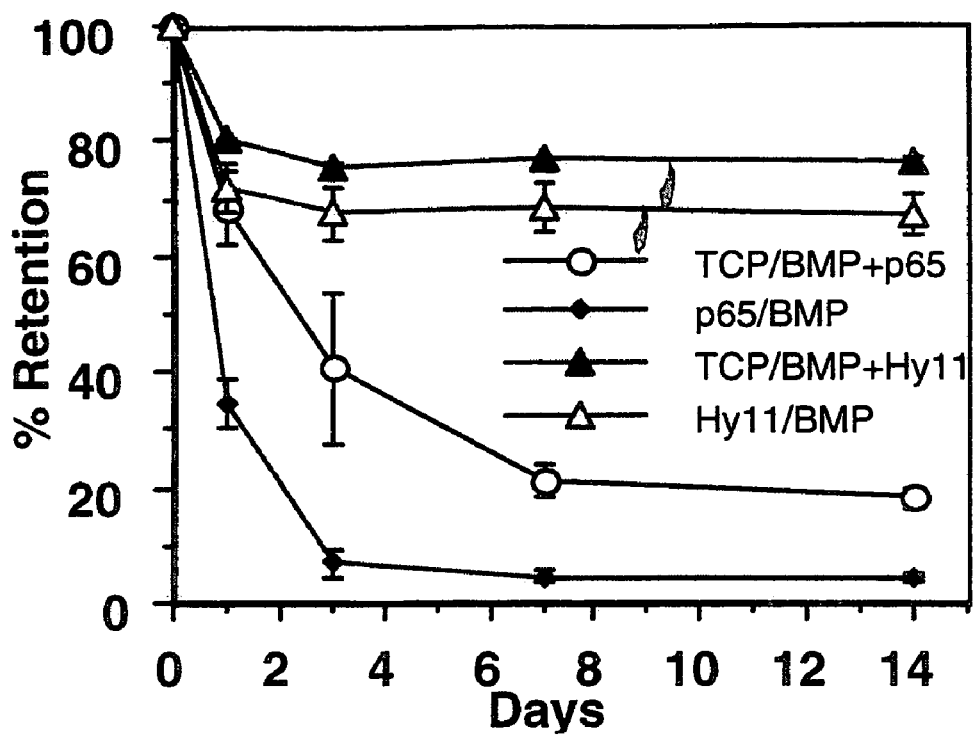
Figure 3. In vitro release kinetics of $^{125}$I-rhBMP-2

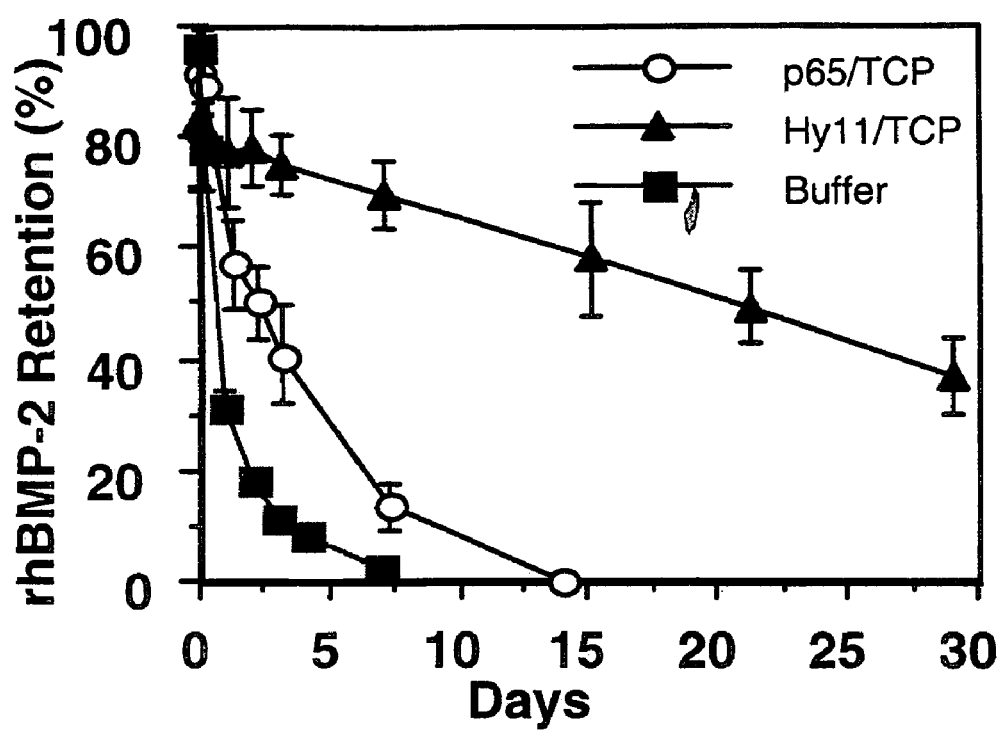
Figure 4. In vivo biodistribution of $^{125}$I-rhBMP-2

INJECTABLE CARRIER FORMULATIONS OF HYALURONIC ACID DERIVATIVES FOR DELIVERY OF OSTEOGENIC PROTEINS

RELATED APPLICATIONS

This application claims the benefit of U.S. Provisional Application No. 60/159,674 filed on Oct. 15, 1999 and U.S. Provisional Application No. 60/185,587 filed on Feb. 28, 2000.

BACKGROUND OF THE INVENTION

The subject invention relates to the field of osteogenic proteins and pharmaceutical formulations thereof. More particularly, the subject invention involves injectable pharmaceutical formulations comprising hyaluronic acid derivatives and osteogenic proteins. The invention further provides methods for formulating porous injectable gels and pastes from hyaluronic acid.

Osteogenic proteins are those proteins capable of inducing, or assisting in the induction of, cartilage and/or bone formation. Many such osteogenic proteins have in recent years been isolated and characterized, and some have been produced by recombinant methods. For example, so-called bone morphogenic proteins (BMP) have been isolated from demineralized bone tissue (see e.g. Urist U.S. Pat. No. 4,455,256); a number of such BMP proteins have been produced by recombinant techniques (see e.g. Wang et al. U.S. Pat. No. 4,877,864 and Wang et al. U.S. Pat. No. 5,013,549); a family of transforming growth factors (TGF-$\alpha$ and TGF-$\beta$) has been identified as potentially useful in the treatment of bone disease (see e.g. Derynck et al., EP 154,434); a protein designated Vgr-1 has been found to be expressed at high levels in osteogenic cells (see Lyons et al. (1989) Proc. Nat'l. Acad. Sci. USA 86, 4554–4558); and proteins designated OP-1, COP-5 and COP-7 have purportedly shown bone inductive activity (see Oppermann, et al. U.S. Pat. No. 5,001,691).

Various formulations designed to deliver osteogenic proteins to a site where induction of bone formation is desired have been developed. For example, certain polymeric matrices such as acrylic ester polymer (Urist, U.S. Pat. No. 4,526,909) and lactic acid polymer (Urist, U.S. Pat. No. 4,563,489) have been utilized.

A biodegradable matrix of porous particles for delivery of an osteogenic protein designated as OP is disclosed in Kuber A. Sampath, U.S. Pat. No. 5,108,753.

Brekke et al., U.S. Pat. Nos. 4,186,448 and 5,133,755 describe methods of forming highly porous biodegradable materials composed of polymers of lactic acid ("OPLA").

Okada et al., U.S. Pat. No. 4,652,441, U.S. Pat. No. 4,711,782, U.S. Pat. No. 4,917,893 and U.S. Pat. No. 5,061,492 and Yamamoto et al., U.S. Pat. No. 4,954,298 disclose a prolonged-release microcapsule comprising a polypeptide drug and a drug-retaining substance encapsulated in an inner aqueous layer surrounded by a polymer wall substance in an outer oil layer.

Yamazaki et al., *Clin. Orthop. and Related Research*, 234:240–249 (1988) disclose the use of implants comprising 1 mg of bone morphogenetic protein purified from bone and 5 mg of Plaster of Paris. U.S. Pat. No. 4,645,503 discloses composites of hydroxyapatite and Plaster of Paris as bone implant materials.

Collagen matrices have also been used as delivery vehicles for osteogenic proteins (see e.g. Jeffries, U.S. Pat. No. 4,394,370).

SUMMARY OF THE INVENTION

The present invention provides injectable formulations for delivery of osteogenic proteins. In one embodiment the composition comprises the osteogenic protein and hyaluronic acid esters. In another embodiment, the composition may further include tricalcium phosphate. The injectable formulations of the invention allows for closed fracture repair and other skeletal tissue without an open reduction procedure as is necessary with implantable devices.

The present invention further provides methods for preparing injectable gels or pastes useful as a carrier for osteogenic proteins by transforming various non-woven pads and sponges of hyaluronic acid benzyl ester into injectable gel or paste formulations by hydration or solvent addition. In another embodiment, the invention comprises compositions comprising the transformed injectable gel or paste formulations.

The methods and compositions of the present invention are useful for the preparation of formulations of osteoinductive proteins which can be used, among other uses, to promote the formation of cartilage and/or bone, for repair of tissue damage and fractures. The invention further provides methods for treating patients in need of cartilage and/or bone repair and/or growth.

BRIEF DESCRIPTION OF THE DRAWINGS

FIG. 1 sets forth in vitro release kinetics of $^{125}$I-rhBMP-2 in Hyaff gels.

FIG. 2 sets forth in vivo retention of $^{125}$I-rhBMP-2 in Hyaff-11/PEG, ACS, and buffer.

FIG. 3 sets forth in vitro release kinetics of $^{125}$I-rhBMP-2 in Hyaff gels/TCP.

FIG. 4 sets forth in vivo biodistribution of $^{125}$I-rhBMP-2.

DETAILED DESCRIPTION OF THE INVENTION

The invention provides injectable formulations for delivery of osteogenic proteins. The compositions comprise an injectable formulation of hyaluronic acid esters and osteogenic protein. The present invention further provides processes for preparing injectable gel or paste formulations by transforming various non-woven pads and sponges of hyaluronic acid benzyl ester by hydration or solvent addition yielding gels with in vivo residence times from days to up to several months. Total or partial esters of hyaluronic acid are described in U.S. Pat. No. 5,336,767. Partial esters of Hyaff solids are transformed into gels using aqueous buffer or organic solvents (such as N-methyl pyrrolidinone, dimethyl sulfoxide, etc), while complete esters of Hyaff solids are transformed into gels using organic solvents. In other embodiments pore formers may be introduced to the solublized carriers to increase porosity. The addition of pore formers would allow in situ pore formation after injection in vivo by solubilization of pore former and precipitation/phase inversion of carrier. Suitable liquid pore formers include polyethylene glycol or PEG at 10–90% volume per volume ratios) and solid pore formers (such as sodium bicarbonate, sodium chloride, citric acid, sucrose, etc., at 1:1–21:1 pore former:Hyaff weight per weight ratios) to increase porosity. The gel/paste can also contain TCP (tri-calcium phosphate) particles as a mineral component for example, at 0.1–100% weight per volume range.

The amount, type and size of the pore forming agent is optimized to leave voids sufficient for cell ingrowth into injectable gel when pore forming agent and solvent are extracted from the carrier in vivo by solubilization of pore forming agent and precipitation/phase inversion of carrier in situ.

The osteogenic proteins useful with the injectable carriers made in accordance with the subject invention are well known to those skilled in the art and include those discussed above. The preferred osteogenic proteins for use herein are those of the BMP class identified as BMP-1 through BMP-12 in U.S. Pat. No. 4,877,864; U.S. Pat. No. 5,013,649; WO 90/11366 published Oct. 4, 1990; WO 91/18098 published Nov. 28, 1991; WO 93/00432, published Jan. 7, 1993; U.S. Ser. Nos. 08/247,908 and 08/247,904, both filed May 20, 1994; and U.S. Ser. No. 08/217,780, filed on Mar. 25, 1994. The disclosure of the above publications are hereby incorporated by reference. The most preferred is BMP-2, the full length cDNA sequence of which is described in detail in the '649 patent. Of course, combinations of two or more of such osteogenic proteins may be used, as may fragments of such proteins that also exhibit osteogenic activity. Such osteogenic proteins are known to be homodimeric species, but also exhibit activity as mixed heterodimers. Heterodimeric forms of osteogenic proteins may also be used in the practice of the subject invention. BMP heterodimers are described in WO93/09229, the disclosure of which is hereby incorporated by reference. Recombinant proteins are preferred over naturally occurring isolated proteins. The amount of osteogenic protein useful herein is that amount effective to stimulate increased osteogenic activity of infiltrating progenitor cells, and will depend upon the size and nature of defect being treated as well as the carrier being employed.

The formulations may be injected for example into tendons, damaged cartilage tissue, ligaments, and/or their attachment sites to bones. Injectable formulations may also find application to other bone sites such as bone cysts, bone defects, intraosseous sites and closed fractures.

The dosage regimen will be determined by the clinical indication being addressed, as well as by various patient variables (e.g. weight, age, sex) and clinical presentation (e.g. extent of injury, site of injury, etc.). In general, the dosage of osteogenic protein will be in the range of from about 0.1 to 4 mg/ml.

The injectable osteogenic protein formulations may be provided to the clinic as a single formulation, or the formulation may be provided as a multicomponent kit wherein, e.g. the osteogenic protein is provided in one vial and the injectable hyaluronic paste is provided separately.

The compositions of the subject invention allow therapeutically effective amounts of osteoinductive protein to be delivered to an injury site where cartilage and/or bone formation is desired. The formulations may be used as a substitute for autologous bone graft in fresh and non-union fractures, spinal fusions, and bone defect repair in the orthopaedic field; in cranio/maxillofacial reconstructions; for prosthesis integration, especially as a surface coating to improve fixation of prosthetic implants such as hydroxyapatite coated prostheses; in osteomyelitis for bone regeneration; and in the dental field for augmentation of the alveolar ridge and periodontal defects and tooth extraction sockets. The methods and formulations of the present invention may be useful in the treatment and/or prevention of osteoporosis, or the treatment of osteoporotic or osteopenic bone. In another embodiment, formulations of the present invention may be used in the process known as distraction osteogenesis. When used to treat osteomyelitis or for bone repair with minimal infection, the osteogenic protein may be used in combination with porous microparticles and antibiotics, with the addition of protein sequestering agents such as alginate, cellulosics, especially carboxymethylcellulose, diluted using aqueous glycerol. The antibiotic is selected for its ability to decrease infection while having minimal adverse effects on bone formation. Preferred antibiotics for use in the devices of the present invention include vancomycin and gentamycin. The antibiotic may be in any pharmaceutically acceptable form, such as vancomycin HCl or gentamycin sulfate. The antibiotic is preferably present in a concentration of from about 0.1 mg/mL to about 10.0 mg/mL. The traditional preparation of formulations in pharmaceutically acceptable form (i.e. pyrogen free, appropriate pH and isotonicity, sterility, etc.) is well within the skill in the art and is applicable to the formulations of the invention.

Hyaluronic derivative compositions of the invention prepared by hydration or solvent addition of insoluble or partially soluble non-woven pads or sponges may also be ultilized in combination with other drugs, growth factors, peptides, proteins, cytokines, oligonucleotides antisense oligonucleotides, DNA and polymers. These compounds may be added by mixing them with the carriers. Or by covalent attachment to the polymer carriers. The hyaluronic derivative compositions may also be used with DNA encoding for BMPs and cells transduced or transfected with genes encoding BMP proteins.

The following examples are illustrative of the present invention and are not limiting in any manner. Modifications, variations and minor enhancements are contemplated and are within the present invention.

EXAMPLE 1

Preparation of Injectable Hyaluronic Acid Esters

The starting Hyaff hyaluronic acid (Fidia Advanced Biopolymers, Abano Terme, Italy) materials are solids such as non-woven pads, felts, sheets, powders, sponges, and microspheres. The Hyaff materials are esters of hyaluronic acid exhibiting various ester moities (e.g., benzyl, ethyl, propyl pentyl or larger molecules such as hydrocortisone or methyl prednislone, etc.) as well as various degrees of esterification (i.e., partial esters or complete esters). Partial esters of Hyaff are designated by percent esterfication ranging from 50–99% (e.g., Hyaff-11p65, Hyaff-11p80, etc.), while complete esters are 100% esters of hyaluronic acid (e.g., Hyaff-11).

Hyaff gel classification used in supporting data is as follows and is followed by examples of select formulations:
- Hyaff-11 gel: Hyaff-11 non-woven pad transformed into gel with organic solvent to yield 10% solids
- Hyaff-11/bicarbonate gel: Hyaff-11 gel mixed with sodium bicarbonate as pore former at 15:1 (w/w) bicarbonate to Hyaff-11
- Hyaff-11/PEG gel: Hyaff-11 gel mixed with polyethylene glycol(200 mw) as pore former at 33–50% (v/v) range
- Hyaff-11/TCP gel: Hyaff-11 gel mixed with 30% w/v TCP
- Hyaff-11/bicarbonate/TCP gel: Hyaff-11/bicarbonate gel mixed with 30% w/v TCP
- Hyaff-11/PEG/TCP gel: Hyaff-11/PEG gel mixed with 30% w/v TCP
- Hyaff-11p80 gel: Hyaff-11p80 non-woven pad transformed into gel with organic solvent to yield 5% solids
- Hyaff-11p65 gel: Hyaff-11p65 non-woven pad hydrated with aqueous buffer to yield 6–15% solids
- Hyaff-11p65/TCP gel: Hyaff-11p65 gel mixed with 30% w/v TCP Hyaff-11p65 non-woven pads were hydrated with glutamic acid buffer (pH 4.5) containing rhBMP-2 (0.1 mg/mL final conc.) to yield either 6%–15% solids (w/v) and mixed thoroughly to form a paste. Hyaff-11p80 and Hyaff-11 non-woven pads were solubilized in N-methyl-pyrrolidinone (NMP) or dimethyl sulfoxide (DMSO) to yield a 1 – 30% w/v solution. These solutions were then mixed with either rhBMP-2-containing buffer (10% v/v, 0.1 mg/mL rhBMP-2), or lyophilized rhBMP-2 (0.1 mg/ML) followed by the addition of various pore formers (polyethylene glycol, sodium bicarbonate, sucrose, NaCl, citric acid) and tricalcium phosphate (TCP). Particle size of solid pore formers and TCP used was <600 um, preferably <200 umLiquid pore formers such as PEG(200 mw) were mixed at 10–90% v/v ratios, and solid pore formers were mixed at 9:1–21:1 (w/w) pore former to carrier ratios. TCP was mixed at 0.1–30% (w/v). TCP (45–125 micron particle size) was mixed thoroughly into rhBMP-2/Hyaff-11 or rhBMP-2/Hyaff-11p65 gel at 30% (w/v). Separately, rhBMP-2 was adsorbed onto TCP first, followed by mixing with Hyaff-11 or Hyaff-11p65 gel. Formulations were chosen based on injectability through an 18 g needle. Microstructure was characterized by scanning electron microscopy (SEM).

SEMS revealed varying degrees of pore structure and porosity. Hyaff-11p65 6% gel exhibited longer fibers than the 15% formulation; with both displaying a high level of porosity. Both Hyaff-11 and Hyaff-11p80 gels showed minimal pore structure and porosity, whereas those carriers with pore formers displayed a high level of porosity. Pore formers and/or additives that yielded injectable mixtures were PEG, sodium bicarbonate and TCP.

EXAMPLE 2

In Vitro Release Kinetics rhBMP-2 was radiolabeled with $^{125}$I using the Iodogen method (Pierce) and used as a tracer for 0.1 mg/ml rhBMP-2 delivered in 100 ul Hyaff-11p65 gel, Hyaff-11p80 gel, Hyaff-11gel and Hyaff-11/PEG (n=4). $^{125}$I-rhBMPhBMP-2 loaded samples (50,000 cpm/sample) were incubated in 1 ml fetal calf serum (Hyclone) at 37° C. on a shaker, and radioactivity of the carrier measured up to 14 days using a gamma counter. Fresh serum was replaced after each time point. $^{125}$I-rhBMPhBMP-2 release from injectable formulations were compared to those of implantable sponges and pads of Hyaff-11 and Hyaff-11p80.

Auto cross-linked polysaccharide form of derivatized hyaluronic acid, ACP gel, is used for the in vitro release study and the rat ectopic assay. For the in vitro release study, 2 ml ACP gel is mixed with 1.53 mg rhBMP-2 cake (which corresponds to 0.2 mg actual rhBMP-2 at 8 mg rhBMP-2 per 61 mg cake weight) and $^{125}$I-rhBMPhBMP-2 (100 μl total, 20 μCi/200 μl gel) and drawn up into 1 ml syringes resulting in approximately 10% gel dilution. ACP gel for the rat ectopic study does not contain the tracer but is diluted with MRF-00906 buffer. 200 μl injections are performed using a 22 gauge needle. The final concentration of rhBMP-2 will be 0.1 mg/ml, or 20 μg per 200 μl injection. The final concentration of $^{125}$I-rhBMP-2 will be approximately 20 μCi per 200 μl injection. The ACP gel will be injected at room temperature.

In vitro release kinetics showed greatest retention of rhBMP-2 over the 2 weeks in the Hyaff-11/PEG gel followed by Hyaff-11p80 gel and Hyaff-11 gel (FIG. 1). Hyaff-11p65 gel released rhBMP-2 the fastest. Sponges and pads of Hyaff-11 and Hyaff-11p80 retained less rhBMP-2 than Hyaff-11/PEG or Hyaff-11p80 gel, but more than Hyaff-11p65. Addition of TCP to Hyaff-11 gel increased rhBMP-2 retention. The release profile in all carriers exhibited moderate to rapid burst release followed by a slow, sustained release of rhBMP-2. All Hyaff-11 and Hyaff-11p80 gel formulations retained rhBMP-2 well (>50% remaining after 14 days) except Hyaff-11p65.

EXAMPLE 3

Rat Ectopic Assay

Hyaff-11 based gels (200 ul/site, n=6) with 0.1 mg/ml rhBMP-2 were injected subcutaneously (ventral thorax) or injected intramuscularly (quadriceps) in 3–4 week old male Long Evans rats. Rats were sacrificed after 2 weeks and bone formation in the explants analyzed histologically using Goldners's trichrome stain. Bone scores (0=no bone, 5=100% bone) were assigned based on histomorphometry. Total bone (mm$^3$) was calculated using explant size and bone score. Radiographs of explants were also taken.

All Hyaff-11 based gels formed significant ectopic bone in the rat model (Table 1) in the presence of rhBMP-2, although differences in bone formation existed between carrier types as confirmed by radiographs and histology. Hyaff-11p65 at varying doses (0.1–1.5 mg/mL) of rhBMP-2 exhibited a dose dependent increase in bone formation (and bone score) but was inconsistent in explant size which yielded less total bone (0.1 mg/mL rhBMP-2 data shown). Hyaff-11p80 explants were large but had a lower bone score, while Hyaff-11 showed good bone score and total bone. Hyaff-11/PEG and Hyaff-11/sodium bicarbonate radiographically showed equivalent radioopacity as those of Hyaff-11 and Hyaff-11p80. Histologically, both Hyaff-11 and Hyaff-11p80 carriers showed residual remaining matrix due to their slow degradation rates, although Hyaff-11p65 completely degraded by 2 weeks. Bone formed within pores, shown by mineralizing osteoblasts as well as through a cartilage intermediate. Addition of TCP to Hyaff-11 gel with or without pore formers also showed comparable radiographic evidence of bone formation as those of other Hyaff based gels.

TABLE 1

Histomorphometry results of rat ectopic bone formation assay.

| Group | Bone score SQ | IM | Total bone SQ | (mm$^3$) IM |
|---|---|---|---|---|
| Hyaff-11p65 | 2.70 | 3.88 | 79 | 172 |
|  | (1.40) | (1.65) | (20) | (33) |
| Hyaff-11p80 | 1.83 | 1.83 | 140 | 314 |
|  | (0.68) | (0.68) | (76) | (179) |
| Hyaff-11 | 2.50 | 3.25 | 228 | 219 |
|  | (1.00) | (0.96) | (132) | (223) |

EXAMPLE 4

In Vivo Biodistribution

Retention of rhBMP-2 within each carrier was analyzed in vivo using a rabbit ulna fracture model. Bilateral 0.5 mm osteotomy defects were created in the ulna of New Zealand White rabbits and 150 uL rhBMP-2/carrier injected into the defect (n=8/group). Gels were loaded with 40 uCi $^{125}$I labeled rhBMP-2 and 0.67 mg/ml unlabeled rhBMP-2.

Amount of radioactivity retained at the fracture site was measured by gamma scintigraphy as a function of time.

In vivo biodistribution of rhBMP-2 from Hyaff-11/PEG gel in the rabbit ulna fracture model showed better retention of rhBMP-2 than absorbable collagen sponge (ACS) and buffer carrier (MFR-842) (FIG. 2). Hyaff-11/PEG retained approximately 40% rhBMP-2 after 7 days. Hyaff-11p65 gel showed poorer retention of rhBMP-2 than Hyaff-11/PEG gel, but displayed comparable fracture callus radiographically.

EXAMPLE 5

In Vitro Release Kinetics rhBMP-2 was radiolabeled with $^{125}$I using the Iodogen method (Pierce) and used as a tracer for 0.1 mg/ml rhBMP-2 delivered in 100 uL Hyaff-11 gel±TCP and Hyaff-11p65 gel±TCP (n=4). $^{125}$I-rhBMP-2 loaded samples (50,000 cpm/sample) were incubated in 1 mL fetal calf serum (Hyclone) at 37° C. on a shaker, and radioactivity of the carrier measured up to 14 days using a gamma counter. Fresh serum was replaced after 1, 3, 7, and 14 days.

Addition of TCP enhanced retention of rhBMP-2 over the course of 2 weeks in both Hyaff-11 and Hyaff-11p65 gels (FIG. 3). Hyaff-11/TCP retained the most rhBMP-2, followed by Hyaff-11, Hyaff-11p65/TCP, and Hyaff-11p65. Hyaff-11 retained more rhBMP-2 than Hyaff-11p65 due to its hydrophobicity and insolubility. Preadsorbing rhBMP-2 on TCP increased rhBMP-2 retention in Hyaff- 11 gel, as opposed to mixing rhBMP-2 into the Hyaff-11 phase. Preadsorbing or mixing rhBMP-2 into either TCP or Hyaff-11p65 phase resulted in similar rhBMP-2 retention, both of which were greater than Hyaff-11p65 without TCP.

EXAMPLE 6

In Vivo Biodistribution and Efficacy

Retention of rhBMP-2 within Hyaff-11/TCP and Hyaff-11p65/TCP was analyzed in vivo using a rabbit ulna fracture model. Bilateral 0.5 mm osteotomy defects were created in the ulna of New Zealand White rabbits (n=3/carrier) and 150 uL carrier or buffer (0.67 mg/mL rhBMP-2) injected around the defect. 20 uCi $^{125}$I-rhBMP-2 was used as a tracer. Amount of radioactivity left within each carrier at the fracture site was measured by gamma scintigraphy over the course of several weeks and in vivo rhBMP-2 retention calculated over time. Fracture repair efficacy was analyzed in these rabbits (n=8) by torsional biomechanical testing after a 4 week sacrifice to obtain maximum torque. Contralateral limbs served as surgical controls.

In vivo retention of rhBMP-2 at the rabbit ulna fracture site showed a similar pattern as that of the in vitro study (FIG. 4). Hyaff-11/TCP gel (rhBMP-2 adsorbed to TCP phase first) exhibited the greatest retention (40% remaining after 4 weeks) followed by Hyaff-11p65/TCP gel (rhBMP-2 undetectable at 14 days) and buffer (undetectable at 7 days). rhBMP-2 accelerated fracture healing when delivered in Hyaff-11p65/TCP or Hyaff-11p65 gel. Maximum torque (N-m) for Hyaff-11p65/TCP and Hyaff-11p65 were significantly greater than their contralateral surgical controls (85.6% and 96.9%, respectively) but not statistically different from each other (Table 1).

TABLE 1

Maximum torque (N-m) of rabbit ulna defects

| Carrier | rhBMP-2 | Control | P value |
|---------|---------|---------|---------|
| P65 | 0.571 ± 0.225 | 0.290 ± 0.158 | 0.0001 |
| P65/TCP | 0.475 ± 0.197 | 0.256 ± 0.087 | 0.0091 |

The foregoing descriptions detail presently preferred embodiments of the present invention. Numerous modifications and variations in practice thereof are expected to occur to those skilled in the art upon consideration of these descriptions. Those modifications are believed to be encompassed within the claims appended hereto.

The invention claimed is:

1. A composition for injectable delivery of osteogenic proteins to a patient comprising
    (a) an osteogenic protein;
    (b) an injectable hyaluronic acid ester; and
    (c) a pore former selected from a liquid pore former or sodium bicarbonate,
    wherein the composition is injectable through the skin of a patient.

2. A composition for injectable delivery of osteogenic proteins to a patient comprising
    (a) an osteogenic protein;
    (b) an injectable hyaluronic acid ester; and
    (c) a pore former selected from a liquid pore former or sodium bicarbonate,
    wherein the composition is injectable through the skin of a patient, and upon injection the osteogenic protein and hyaluronic acid ester form a porous precipitate.

3. A composition for injectable delivery of osteogenic proteins to a patient comprising
    (a) an osteogenic protein;
    (b) an injectable hyaluronic acid ester; and
    (c) a pore former selected from a liquid pore former or sodium bicarbonate,
    wherein the composition is injectable through the skin of a patient, and upon injection the pore former is extracted from the osteogenic protein and hyaluronic acid ester by solubilization in situ.

4. The composition of any one of claims 1 to 3, wherein the hyaluronic acid ester is at least 50% esterified.

5. The composition of any one of claims 1 to 3, wherein the hyaluronic acid ester is at least 60% esterified.

6. The composition of any one of claims 1 to 3, wherein the hyaluronic acid is at least 65% esterified.

7. The composition of any one of claims 1 to 3, wherein the hyaluronic acid is at least 75% esterified.

8. The composition of any one of claims 1 to 3, wherein the hyaluronic acid is at least 80% esterified.

9. The composition of any one of claims 1 to 3, wherein the hyaluronic acid is 100% esterified.

10. The composition of any one of claims 1 to 3, wherein the liquid pore former is polyethylene glycol.

11. The composition of any one of claims 1 to 3, wherein the hyaluronic acid ester is solubilized in an organic solvent.

12. The composition of any one of claims 1 to 3, wherein the hyaluronic acid ester is solubilized in an aqueous buffer.

13. The composition of any one of claims 1 to 3, further comprising TCP.

14. The composition of any one of claims 1 to 3, wherein the osteogenic protein is selected from the group consisting of BMP-2, BMP-4, BMP-5, BMP-6, BMP-7, BMP-8, BMP-9, BMP-10, BMP-11, and BMP-12.

15. The composition of any one of claims 1 to 3, wherein the hyaluronic acid ester is Hyaff11.

16. The composition of claim 15, wherein the liquid pore former Is polyethylene glycol.

17. The composition of claim 15, wherein the hyaluronic acid ester is solubilized in an organic solvent.

18. The composition of claim 15, further comprising TCP.

19. The composition of claim 15, wherein the osteogenic protein is selected from the group consisting of BMP-2, BMP-4, BMP-5, BMP-6, BMP-7, BMP-8, BMP-9, BMP-10, BMP-11, and BMP-12.

20. The composition of any one of claims 1 to 3, wherein the hyaluronic acid ester is Hyaff11p80.

21. The composition of claim 20, wherein the liquid pore former is polyethylene glycol.

22. The composition of claim 20, wherein the hyaluronic acid ester is solubilized in an organic solvent.

23. The composition of claim 20, further comprising TCP.

24. The composition of claim 20, wherein the osteogenic protein Is selected from the group consisting of BMP-2, BMP-4, BMP-5, BMP-6, BMP-7, BMP-8, BMP-9, BMP-10, BMP-11, and BMP-12.

25. A composition for delivery of osteogenic proteins to a patient comprising an osteogenic protein and Hyaff11p65, wherein the composition is injectable through the skin of the patient.

26. The composition of claim 25, wherein the osteogenic protein is selected from the group consisting of BMP-2, BMP-4, BMP-5, BMP-6, BMP-7, BMP-8, BMP-9, BMP-10, BMP-11, and BMP-12.

27. The composition of claim 25, wherein the Hyaff11p65 is solubilized in aqueous buffer.

28. The composition of claim 25, further comprising TCP.

29. A composition for delivery of osteogenic proteins to a patient comprising BMP-12 and Hyaff11p65, wherein the composition is injectable through the skin of the patient.

* * * * *